(12) United States Patent
Zemenchik (10) Patent No.: US 9,516,802 B2
(45) Date of Patent: Dec. 13, 2016

(54) SYSTEM AND METHOD FOR CONTROLLING AN AGRICULTURAL SYSTEM BASED ON SOIL ANALYSIS

(71) Applicant: CNH Industrial America LLC, New Holland, PA (US)

(72) Inventor: Robert A. Zemenchik, Kenosha, WI (US)

(73) Assignee: CNH Industrial America LLC, New Holland, PA (US)

( * ) Notice: Subject to any disclaimer, the term of this patent is extended or adjusted under 35 U.S.C. 154(b) by 0 days.

(21) Appl. No.: 14/695,454

(22) Filed: Apr. 24, 2015

(65) Prior Publication Data

US 2015/0305228 A1  Oct. 29, 2015

Related U.S. Application Data

(60) Provisional application No. 61/984,471, filed on Apr. 25, 2014.

(51) Int. Cl.
*A01B 79/00* (2006.01)
*A01B 71/02* (2006.01)
(Continued)

(52) U.S. Cl.
CPC ............... *A01B 71/02* (2013.01); *A01B 63/32* (2013.01); *A01B 67/00* (2013.01); *A01B 76/00* (2013.01);
(Continued)

(58) Field of Classification Search
CPC ..... A01B 79/005; A01B 69/008; A01B 49/06; A01B 19/00; A01B 35/28; A01B 35/32; A01B 63/26; A01B 63/32; A01C 21/002; A01C 15/00; A01C 23/023; A01C 23/024; A01C 21/005; A01C 23/007; A01C 23/008; A01C 5/062; A01C 23/04; A01C 23/042; A01C 23/047; A01C 5/06; A01C 7/00; A01C 7/085; A01C 7/102; A01C 7/20; G05D 1/0088; G05D 1/0011; G05D 1/0231; Y02P 60/214; Y02P 60/215; B25J 5/00; B64C 2201/12; B64C 2201/141; B64C 39/024; Y10S 901/01
(Continued)

(56) References Cited

U.S. PATENT DOCUMENTS 4,674,578 A    6/1987  Bexten et al.
5,033,397 A    7/1991  Colburn, Jr.
(Continued)

FOREIGN PATENT DOCUMENTS

CN    202421071 U    9/2012
EP    0615682 A1    9/1994
(Continued)

OTHER PUBLICATIONS

Adamchuk, Viacheslav I.; Precision Agriculture: Does It Make Sense?; Better Crops/vol. 94 (2010, No. 3);pp. 4-6; http://www.ipni.net/publication/bettercrops.nsf/0/DD1B3874E030BC1485257980006039BF/$FILE/Better%20Crops%202010-3%20p4-6.pdf; accessed Jul. 20, 2015.
(Continued)

*Primary Examiner* — Behrang Badii
*Assistant Examiner* — Sanjeev Malhotra
(74) *Attorney, Agent, or Firm* — Rebecca L. Henkel (57) ABSTRACT

An agricultural system includes an agricultural soil analyzer positioned forward of a ground engaging tool relative to a direction of travel of the agricultural system. The agricultural soil analyzer is configured to output a first signal indicative of a parameter of soil forward of the soil conditioner relative to the direction of travel. The agricultural system also includes a controller communicatively coupled
(Continued)

to the agricultural soil analyzer. The controller is configured to receive the first signal from the agricultural soil analyzer. Furthermore, the controller is configured to determine a target parameter of the agricultural system based on the first signal and to output a second signal indicative of the target parameter.

8 Claims, 6 Drawing Sheets

(51) Int. Cl.
| | | |
|---|---|---|
| A01C 7/10 | (2006.01) | |
| A01C 21/00 | (2006.01) | |
| A01B 76/00 | (2006.01) | |
| G01N 27/02 | (2006.01) | |
| G01N 33/24 | (2006.01) | |
| A01B 63/32 | (2006.01) | |
| A01B 67/00 | (2006.01) | |
| A01G 25/16 | (2006.01) | |
| G01V 3/15 | (2006.01) | |

(52) U.S. Cl.
CPC ............ *A01B 79/005* (2013.01); *A01C 7/102* (2013.01); *A01C 21/005* (2013.01); *G01N 27/028* (2013.01); *G01N 33/24* (2013.01); *A01G 25/167* (2013.01); *G01N 2033/245* (2013.01); *G01V 3/15* (2013.01); *Y02P 60/214* (2015.11)

(58) Field of Classification Search
USPC ..... 701/2, 23, 25; 172/1, 2, 3, 66, 311, 614, 172/664, 705; 705/28; 111/14, 69, 119, 120, 111/121, 139, 149, 200; 56/10.2 A, 10.2 R, 98, 56/314; 460/4, 99; 280/124.104; 239/11, 172
See application file for complete search history.

(56) References Cited

U.S. PATENT DOCUMENTS

| | | | |
|---|---|---|---|
| 5,394,949 A | 3/1995 | Wright et al. | |
| 5,425,427 A | 6/1995 | Haugen | |
| 5,479,992 A | 1/1996 | Bassett | |
| 5,524,560 A | 6/1996 | Carter | |
| 5,663,649 A | 9/1997 | Topp et al. | |
| 6,016,713 A | 1/2000 | Hale | |
| 6,041,582 A * | 3/2000 | Tiede | A01B 79/005 56/10.2 A |
| 6,608,672 B1 | 8/2003 | Shibusawa et al. | |
| 6,937,939 B1 | 8/2005 | Shibusawa et al. | |
| 7,068,051 B2 | 6/2006 | Anderson | |
| 7,216,555 B2 | 5/2007 | Drummond et al. | |
| 7,254,485 B2 | 8/2007 | Rooney et al. | |
| 8,011,439 B2 | 9/2011 | Gadzella et al. | |
| 8,204,689 B2 | 6/2012 | Christy et al. | |
| 8,451,449 B2 | 5/2013 | Holland | |
| 8,768,667 B2 | 7/2014 | Lindores | |
| 2002/0082062 A1* | 6/2002 | Sheidler | A01F 7/065 460/99 |
| 2005/0022707 A1* | 2/2005 | Cresswell | A01C 5/06 111/200 |
| 2005/0172733 A1 | 8/2005 | Drummond et al. | |
| 2006/0000622 A1* | 1/2006 | Cresswell | A01C 5/06 172/705 |
| 2006/0027988 A1* | 2/2006 | Bordini | B60G 3/12 280/124.104 |
| 2006/0108127 A1* | 5/2006 | Batthala | A01B 63/1117 172/2 |
| 2007/0245939 A1* | 10/2007 | Gehrer | A01C 5/062 111/170 |
| 2007/0250412 A1* | 10/2007 | Anderson | G06Q 10/00 705/28 |
| 2008/0047475 A1 | 2/2008 | Stehling et al. | |
| 2009/0020053 A1* | 1/2009 | Bourgault | A01B 61/00 111/69 |
| 2010/0071336 A1* | 3/2010 | Christensen | A01D 45/023 56/98 |
| 2010/0263579 A1* | 10/2010 | Dillon | A01B 35/28 111/139 |
| 2010/0283603 A1 | 11/2010 | Yule et al. | |
| 2011/0113996 A1* | 5/2011 | Mariman | A01C 5/066 111/149 |
| 2011/0153168 A1 | 6/2011 | Peterson et al. | |
| 2011/0153169 A1 | 6/2011 | Peterson | |
| 2012/0037057 A1* | 2/2012 | Beaujot | A01C 7/088 111/14 |
| 2012/0061111 A1* | 3/2012 | Dillon | A01B 35/28 172/66 |
| 2012/0227992 A1 | 9/2012 | Henry | |
| 2013/0146317 A1* | 6/2013 | Wendte | A01B 35/20 172/1 |
| 2013/0184944 A1 | 7/2013 | Missotten et al. | |
| 2013/0233088 A1 | 9/2013 | Noble et al. | |
| 2013/0319699 A1* | 12/2013 | Kromminga | A01B 49/02 172/149 |
| 2013/0325242 A1* | 12/2013 | Cavender-Bares | A01C 21/002 701/25 |
| 2014/0048001 A1 | 2/2014 | Bassett | |
| 2014/0048296 A1 | 2/2014 | Bassett | |
| 2014/0060404 A1* | 3/2014 | Blunier | A01C 23/008 111/119 |
| 2014/0060405 A1* | 3/2014 | Blunier | A01C 23/007 111/120 |
| 2014/0060406 A1* | 3/2014 | Blunier | A01C 23/025 111/121 |
| 2014/0060861 A1* | 3/2014 | Blunier | A01B 73/046 172/1 |
| 2014/0060866 A1* | 3/2014 | Blunier | A01B 73/04 172/311 |
| 2014/0060871 A1* | 3/2014 | Blunier | A01B 61/04 172/614 |
| 2014/0083341 A1* | 3/2014 | Arksey | A01B 3/00 111/120 |
| 2014/0116020 A1* | 5/2014 | Mossman | A01D 63/04 56/314 |
| 2014/0116736 A1* | 5/2014 | Dietrich, Sr. | A01B 61/044 172/664 |
| 2014/0131469 A1* | 5/2014 | Henry | B05B 1/3046 239/11 |
| 2014/0206421 A1* | 7/2014 | Kile | A01F 12/58 460/4 |
| 2014/0250849 A1* | 9/2014 | Ritter | A01D 75/182 56/10.2 R |
| 2014/0261115 A1* | 9/2014 | Kowalchuk | A01C 7/046 111/120 |
| 2014/0326804 A1* | 11/2014 | Mangen | A01G 25/09 239/172 |
| 2015/0051779 A1* | 2/2015 | Camacho-Cook | A01B 69/008 701/23 |
| 2015/0142250 A1* | 5/2015 | Cavender-Bares | A01C 7/00 701/23 |
| 2015/0189829 A1* | 7/2015 | Blunier | A01C 23/007 111/120 |
| 2015/0230399 A1* | 8/2015 | Blunier | A01B 49/06 111/121 |
| 2015/0237791 A1* | 8/2015 | Bassett | A01B 51/02 172/3 |
| 2016/0124433 A1* | 5/2016 | Cavender-Bares | A01C 7/00 701/2 |
| 2016/0157415 A1* | 6/2016 | Cavender-Bares | A01C 21/002 701/23 |

FOREIGN PATENT DOCUMENTS

| | | |
|---|---|---|
| EP | 1241488 A2 | 9/2002 |
| EP | 2586634 A1 | 5/2013 |

(56) References Cited

FOREIGN PATENT DOCUMENTS

| JP | S6474912 | 3/1989 |
|---|---|---|
| WO | 02/49414 A1 | 6/2002 |
| WO | 2013131882 A2 | 9/2013 |

OTHER PUBLICATIONS

Adamchuk, Viacheslav I.; On-the-Go Proximal Soil Sensing for Agriculture; Feb. 21, 2011; http://adamchukpa.mcgill.ca/presentations/Agri-Sensing_2011.pdf; accessed Jul. 20, 2015.

Gunzenhauser, Bob; Shanahan, John; and Lund, Eric; Crop Insights: Utilizing On-the Go Soil Sensing Devices to Improve Definition of Management Zones; https://www.pioneer.com/home/site/us/agronomy/soil-sensing-mgmt-zones/; accessed Jul. 20, 2015.

Grift, Tony E.; Kasten, Matthias; and Nagasaka, Yoshida; Development of Autonomous Robots for Agricultural Applications; http://abe-research.illinois.edu/faculty/grift/research/biosystemsautomation/agrobots/RoboticsUIUC_CropProtectionConf.pdf; accessed Jul. 20, 2015.

University of Nebraska-Lincoln; Soil Sensing; CropWatch; 2014; http://cropwatch.unl.edu/ssm/sensing; accessed Jul. 20, 2015.

Dualem-21S; http://www.dualem.com/products.html; accessed Jul. 20, 2015.

Geonics EM38-MK2 Ground Conductivity Meter; 2013; http://www.geonics.com/html/em38.html; accessed Jul. 20, 2015.

Reese Towpower One Wrench Tightening System; http://www.cequentconsumerproducts.com/_literature_104080/Interlok_-_One_Wrench_Tightening_System; accessed Jul. 21, 2015.

Adamchuk, Viacheslav I.; Hummel, J.W.; Morgan, M.T.; and Upadhyaya, S. K.; On-the-go Soil Sensors for Precision Agriculture; Biological Systems Engineering: Papers and Publication, University of Nebraska-Lincoln; Jun. 14, 2004.

Knight, Quenten; Electromagnetic Soil Mapping—Implementing the Outcomes; 5th Australian Controlled Traffic and Precision Agriculture Conference, University of Western Australia; Jul. 16-18, 2007; pp. 89-97.

U.S. Appl. No. 14/695,945, filed Apr. 24, 2015, Robert A. Zemenchik.

U.S. Appl. No. 14/695,753, filed Apr. 24, 2015, Robert A. Zemenchik.

Sattler, Claudia, Teilflachenspezifische Bewirtschaftung, Ein Konzept zur Integration Von Umwelt-und Naturschutzzielen in die Nutzung landwirtschaftlicher Produktionsflachen, Feb. 1, 2002, pp. 1-4.

Scholderle, Florian et al., Multi Sensor System Requirements for a Position Steered Seed Deposition in Sugar Beet Cultivation for the Generation of a Rectangular Formation, Jan. 1, 2008, pp. 1-11.

Grisso, Robert et al., Precision Farming Tools: Variable-Rate Application, Virginia Cooperative Extension, Jan. 1, 2011, pp. 1-16.

Koch, Julia, Schlaue Schlepper, Agraringenieure Entwickeln den Traktor der Zukunft: Mit Hilfe von Satelliten und Hightech-Sensoren Soli er Kunftig Jedes Pflanzchen Personlich Umsorgen, Technik, Aug. 23, 2010, p. 133.

International Search Report and Written Opinion for International Application No. PCT/US2015/027617 mailed on Jul. 23, 2015.

International Search Report and Written Opinion for International Application No. PCT/US2015/027602 mailed on Jul. 3, 2015.

International Search Report and Written Opinion for International Application No. PCT/US2015/027629 mailed on Jul. 23, 2015.

\* cited by examiner

SYSTEM AND METHOD FOR CONTROLLING AN AGRICULTURAL SYSTEM BASED ON SOIL ANALYSIS

CROSS REFERENCE TO RELATED APPLICATIONS

This application claims priority from and the benefit of U.S. Provisional Application Ser. No. 61/984,471, entitled "System for Mounting an Agricultural Soil Analyzer to Agricultural Implement", filed Apr. 25, 2014, which is hereby incorporated by reference.

BACKGROUND

The invention relates generally to agricultural systems and, more particularly, to a system and method for controlling an agricultural system based on soil analysis.

Certain agricultural operators may conduct soil analysis before beginning planting operations in agricultural fields. Soil analysis may facilitate in planning of planting operations, thereby increasing yield and/or planting efficiency. For example, an analysis identifying specific areas having a rough or uneven soil surface may influence soil conditioning operations in the specific areas. In addition, operators may reduce waste and save time by limiting planting and/or conditioning to desirable areas of an agricultural field. Moreover, unwanted compaction of the soil may be reduced by performing fewer passes in the agricultural field. Furthermore, reducing the time between analysis and conditioning may improve surface quality. However, typical soil analysis may be time consuming, expensive, and data intensive.

BRIEF DESCRIPTION

In one embodiment, an agricultural system includes a ground engaging tool configured to engage an agricultural field. The agricultural system also includes an agricultural soil analyzer positioned forward of the ground engaging tool relative to a direction of travel of the agricultural system. The agricultural soil analyzer is configured to output a first signal indicative of a parameter of soil forward of the ground engaging tool relative to the direction of travel. Also, the agricultural system includes a controller communicatively coupled to the agricultural soil analyzer. The controller is configured to receive the first signal from the agricultural soil analyzer. Moreover, the controller is configured to determine a target speed of the agricultural system based on the first signal and to output a second signal indicative of the target speed, to determine a target pressure of the ground engaging tool based on the first signal and to output a third signal indicative of the target pressure, to determine a target penetration depth of the ground engaging tool based on the first signal and to output a fourth signal indicative of the target penetration depth, or a combination thereof.

In another embodiment, a method of controlling an agricultural system, includes receiving a first signal from a soil analyzer indicative of a surface roughness of soil forward of a soil conditioner relative to a direction of travel of the agricultural system. The soil conditioner is configured to apply a pressure to a surface of a field. The method also includes determining a target pressure of the soil conditioner based on the first signal. The method further includes outputting a second signal to a soil conditioner controller indicative of the target pressure. The soil conditioner controller is configured to adjust the pressure of the soil conditioner based on the target pressure.

In another embodiment, an agricultural system includes an agricultural soil analyzer positioned forward of a ground engaging tool relative to a direction of travel of the agricultural system. The agricultural soil analyzer is configured to output a first signal indicative of a parameter of soil forward of the soil conditioner relative to the direction of travel. The agricultural system also includes a controller communicatively coupled to the agricultural soil analyzer. The controller is configured to receive the first signal from the agricultural soil analyzer. Furthermore, the controller is configured to determine a target parameter of the agricultural system based on the first signal and to output a second signal indicative of the target parameter.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of operating parameters and/or environmental conditions are not exclusive of other parameters/conditions of the disclosed embodiments.

The embodiments described herein relate to a system and method for controlling an agricultural system based on soil roughness data from a soil analyzer. In certain embodiments, the soil analyzer may be a soil analyzer configured to emit acoustic waves against the soil surface and receive backscattered or reflected waves. Thereafter, a processor may evaluate the returned acoustic waves to determine a parameter of the soil, such as the roughness of the soil surface. Based on the surface roughness, a controller may send a signal to a ground engaging tool (e.g., a soil conditioner, a tillage implement, etc.) to adjust an operating parameter (e.g., to increase the pressure a rolling basket applies to the soil surface) to enhance soil preparation. In other embodiments, the controller may send a signal to the agricultural system to control the speed of the agricultural system based on the surface roughness. In certain embodiments, the soil analyzer is mounted on a mounting assembly configured to move the soil analyzer between a stored position and an operation position. While in the stored position, the analyzer may be located proximate to a front end or a rear end of a tow vehicle. However, in the operation position, the analyzer extends longitudinally in front of or behind the tow vehicle and proximate to the soil surface. Accordingly, the soil analyzer is in front of the soil conditioner. An operator may lower the soil analyzer into the operation position, thereby enabling the soil analyzer to determine surface roughness. The control system may then adjust the operating pressure of the soil conditioner and/or adjust the speed of the agricultural system to enhance field preparation.

Soil analysis may be conducted in a variety of ways. For example, soil samples may be removed from an agricultural field and analyzed in a laboratory setting. Additionally, non-contact and/or soil surface sensors may be used to obtain various soil properties while reducing disturbance of the agricultural field. Typically, when using non-contact sensors, operators conduct soil analysis separately from planting, fertilizing, and/or tillage operations. For example, one pass may be used to conduct soil analysis, in which the operator tows equipment over the agricultural field to obtain data for evaluation. The data may then be evaluated to generate soil maps or yield maps indicating a variety of field properties. The soil maps may be used to direct future planting, fertilizing, and/or tillage operations. Then, subsequent passes may be used to condition the soil, fertilize the soil, and/or deposit seeds into the soil. During the planting, fertilizing, and/or tillage process, the operator may consult the soil maps to adjust planting rates, fertilizing rates, and/or tillage operations based on the properties obtained from the soil analysis. Using multiple passes increases the cost and the time it takes for operators to condition, fertilize, and plant the field. Combining the soil analysis and conditioning processes obviates at least one field pass that operators may make when preparing fields for planting. Moreover, by conducting soil analysis closer to actual planting operations, current data related to soil conditions is generated, such as roughness, salinity, cation exchange capacity, clay content, or the like. As a result, efficiency may be increased, along with yields.

Figure 1:
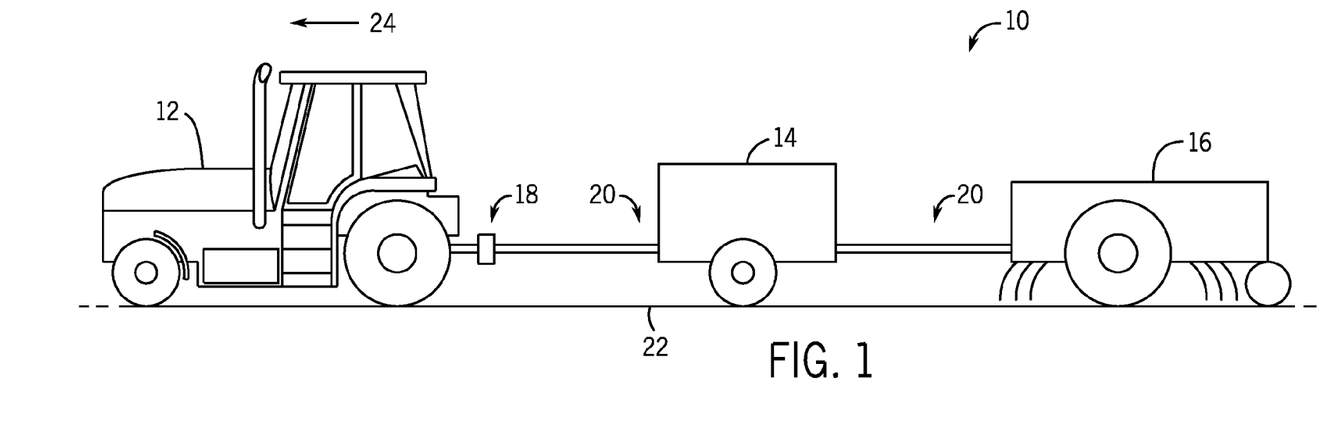
FIG. 1 is a side view of an embodiment of an agricultural system, including a tow vehicle, a soil analyzer assembly, and an agricultural implement.

FIG. 1 is a side view of an agricultural system 10. The agricultural system 10 includes a tow vehicle 12, a soil analyzer assembly 14 (e.g., assembly, analyzer assembly, etc.), and an agricultural implement 16. The tow vehicle 12 may be any vehicle suitable for towing the agricultural implement 16, such as a tractor, off-road vehicle, work vehicle, and the like. Additionally, although the illustrated implement is a stand-alone soil conditioner, the agricultural implement 16 may be any implement, such as a ground engaging implement (e.g., the soil conditioner, a tillage implement, a fertilizer implement, a planter, etc.), suitable for agricultural use.

In the illustrated embodiment, the soil analyzer assembly 14 is coupled to the tow vehicle 12 via a hitch 18. Furthermore, as described in detail below, the agricultural implement 16 is attached to the tow vehicle 12 via a frame 20. The agricultural system 10 travels over a surface 22, such as the ground, a road, a field, or another surface. The tow vehicle 12 is configured to drive the agricultural implement 16 in a direction of travel 24. Moreover, in certain embodiments, the soil analyzer assembly 14 may be mounted to the front of the tow vehicle 12 and/or to the front of the agricultural implement 16. As will be discussed in detail below, by mounting the assembly 14 in front of the agricultural implement 16, conditioning of the undisturbed field (e.g., untilled, unconditioned, etc.) may be obtained and used to modify operating parameters of the agricultural implement 16. For example, in certain embodiments, a controller may receive data acquired by the soil analyzer and relay operating instructions to the agricultural implement 16 to enhance field preparations based on the data. For instance, a pressure applied by a rolling basket mounted to the agricultural implement 16 may be adjusted based on a roughness of the soil surface forward of the rolling basket. Additionally, the penetration depth of tillage discs may be adjusted based on the data acquired by the soil analyzer. Moreover, in certain embodiments, a speed of the tow vehicle 12 may be adjusted based on the roughness of the soil surface forward of the tow vehicle 12 and/or forward of the rolling basket.

Figure 2:
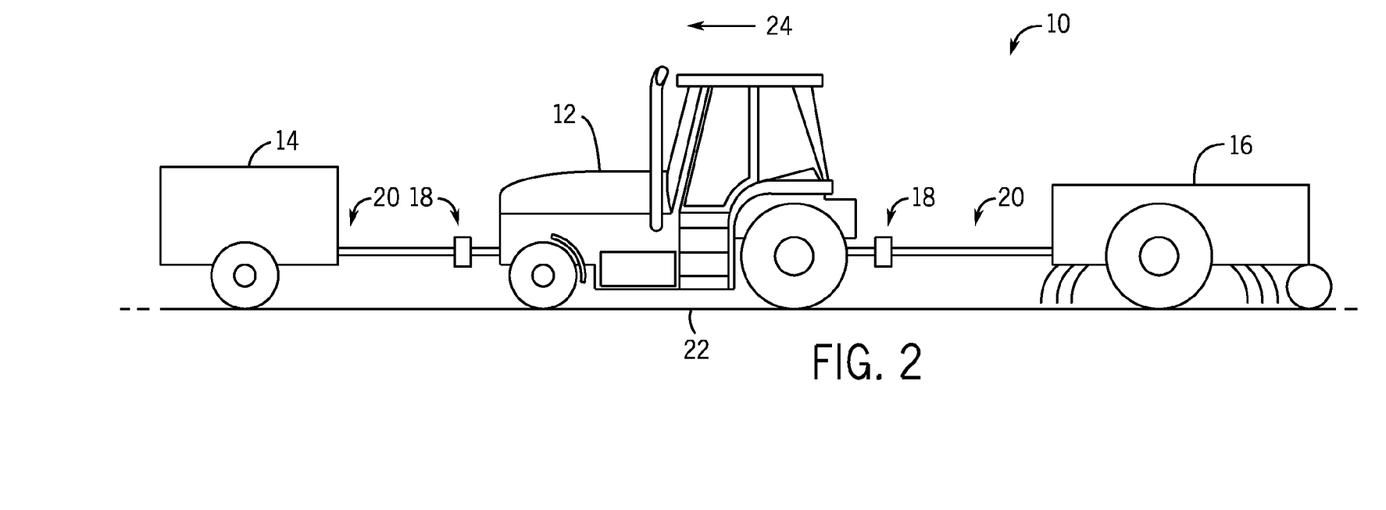
FIG. 2 is a side view of another embodiment of an agricultural system, including a soil analyzer mounted forward of a tow vehicle and an agricultural implement mounted rearward of the tow vehicle.

FIG. 2 is a perspective view of an alternative embodiment of the soil analyzer assembly 14 coupled to the front end of the tow vehicle 12. As shown, the hitch 18 is mounted on a front end of the tow vehicle 12. It will be appreciated that while the foregoing embodiments depict the soil analyzer assembly 14 as an attached implement with wheels, in certain embodiments the assembly 14 may be coupled to the hitch 18 and/or to the agricultural implement 16 with a different support structure (e.g., wheels, a sled, a frame, etc.). For example, as will be discussed below, the assembly 14 may include a support wheel or a sled to support the weight of the assembly 14 as the assembly 14 is moved through a field. However, in certain embodiments, a separate support structure may be omitted. For instance, the assembly 14 may be coupled to and supported by the tow vehicle 12 and/or agricultural implement 16. For example, the assembly 14 may include at least one soil analyzer positioned on a front end of the agricultural implement 16. The soil analyzer may be fully supported by the agricultural implement 16, and as a result the analyzer assembly 14 may include the soil analyzer without additional support structures. Moreover, as described above, in certain embodiments, the soil analyzer may be coupled directly to the tow vehicle 12 without additional support structures.

Figure 3:
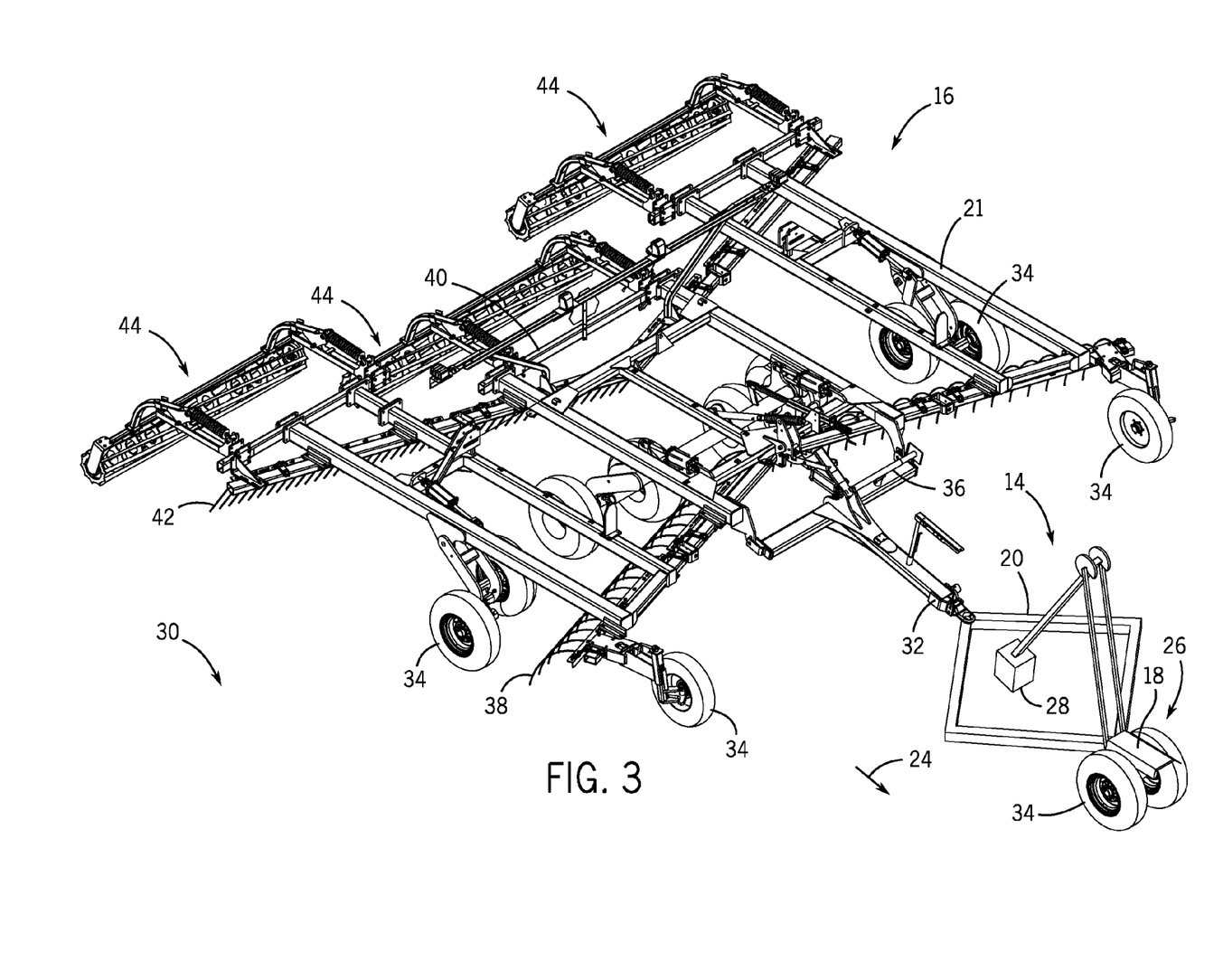
FIG. 3 is a perspective view of an embodiment of an agricultural implement, including a soil analyzer assembly.

FIG. 3 is a perspective view of an embodiment of the soil analyzer assembly 14 coupled between the tow vehicle 12 and the agricultural implement 16. In the illustrated embodiment, the soil analyzer assembly 14 includes a mounting assembly 26 coupled to the hitch 18. As shown, the frame 20 of the soil analyzer assembly 14 has a generally quadrilateral shape. However, it will be appreciated that other shapes may be utilized to support the mounting assembly 26 and a soil analyzer 28 (e.g., probe, meter, detector, analyzer, etc.) while enabling movement of the mounting assembly 26 from a stored position to an operation position. As will be discussed in detail below, the frame 20 includes an opening or gap to enable the mounting assembly 26 to lower the soil analyzer 28 toward the surface 22 of an agricultural field 30. In other words, the frame 20 of the soil analyzer assembly 14 is configured to support the mounting assembly 26 while the mounting assembly 26 is in the stored position and in the operation position. Furthermore, the frame 20 of the assembly 14 is configured to enable the agricultural implement 16 to couple to the assembly 14 (e.g., via a hitch).

As mentioned above, in certain embodiments, the mounting assembly 26 may be coupled to a hitch at the front end of the tow vehicle 12. The mounting assembly 26 is configured to support the soil analyzer 28. However, as mentioned above, in certain embodiments, the soil analyzer 28 may be coupled directly to the agricultural implement 16 (e.g., without the frame 20 and the mounting assembly 26). In the illustrated embodiment, the soil analyzer 28 includes an acoustic transducer (e.g., acoustic wave emitter and receiver) configured to interrogate the surface 22 of the agricultural field 30 with acoustic waves at a desired frequency. Acoustic waves may be "backscattered" or "bounced" off of the surface 22 back toward the analyzer 28. Accordingly, the soil analyzer 28 may receive and record the waves returned from the surface 22. However, in other embodiments, the soil analyzer 28 may be a camera, a chemical analyzer, an optical analyzer, an electromagnetic analyzer, or the like. As will be described in detail below, the data received by the soil analyzer 28 may be analyzed by a controller to determine the roughness of the surface 22 and to generate two-dimensional or three-dimensional soil maps of the agricultural field. In certain embodiments, the data may be analyzed in real-time or near real-time to control field conditioning operations. For example, the data received by the soil analyzer 28 may be used to control a pressure applied by a rolling basket the surface 22 during soil preparation operations. Additionally, in other embodiments, the data received by the soil analyzer 28 may be used to control the pressure (e.g., aggressiveness) of a row cleaner. In certain embodiments, multiple soil analyzers 28 may be utilized to control the pressure applied by multiple rolling baskets. For example, each rolling basket may be associated with one soil analyzer 28, which is configured to control operation of the respective rolling basket. Additionally, each rolling basket may be associated with multiple soil analyzers 28. Moreover, in certain embodiments, each soil analyzer 28 may be associated with multiple rolling baskets. By employing multiple soil analyzers, better resolution of soil conditions may be obtained by individually analyzing different swaths of soil. In addition, by utilizing individually controllable rolling baskets, each swatch may be conditioned based on the particular soil conditions of the swath.

The soil analyzer 28 is a non-contact analyzer (e.g., soil surface sensor; low disruption or compaction sensor, etc.) that is configured to be positioned proximate (e.g., proximal) to the agricultural field 30 while obtaining data. As used herein, proximate refers to above or at the soil surface. In certain embodiments, proximate may refer to a distance that does not contact the surface 22 but is close enough to facilitate accurate measurements. For example, the analyzer 28 may be six inches, twelve inches, twenty four inches, or any suitable distance from the surface 22 as long as the emitted acoustic waves are able to reach the surface 22 and the resulting backscattered waves are able to return to the analyzer 28. However, in other embodiments, the analyzer 28, or components coupled to the analyzer 28, may contact the surface 22. Moreover, as discussed in detail below, the analyzer 28 includes integrated electronic/software components or systems including a global positioning system (GPS), data acquisition software, and the like.

As will be described in detail below, the mounting assembly 26 is configured to extend and retract between a first position (e.g., a stored position) and a second position (e.g., an operation position). In the illustrated embodiment, the analyzer 28 is in the first position longitudinally proximate to the rear end of the tow vehicle 12. However, while in the second position, the analyzer 28 is positioned longitudinally rearward of the first position, relative to the direction of travel 24 of the agricultural system 10. Moreover, while in the second position, the analyzer 26 is positioned proximate to the surface of the agricultural field 30. In certain embodiments, as described above, the analyzer 28 may be mounted to the front of the tow vehicle 12. Accordingly, the analyzer may be longitudinally proximate to the front end of the tow vehicle 12 while in the first position and longitudinally forward of the first position, relative to the direction of travel 24, while in the second position.

In the illustrated embodiment, the agricultural implement 16 is coupled to the soil analyzer assembly 14 via a hitch assembly 32. As shown, the agricultural implement 16 is a stand-alone soil conditioner. However, in alternative embodiments, the agricultural implement 16 may be a field cultivator, a fertilizer applicator, a planter, or the like (e.g., including a ground engaging implement). The implement 16 is configured to be towed behind the tow vehicle 12, in the direction of travel 24. The implement 16 includes wheels 34 which are used to guide the implement 16 along the surface 22 of the agricultural field 30. As mentioned above, the implement 16 is attached to the soil analyzer assembly 14 via the hitch assembly 32. However, in certain embodiments, the soil analyzer 28 of the soil analyzer assembly 14 may be directly coupled to the implement 16. In certain embodiments, the hitch assembly 32 is connected via bolts or other suitable couplings to an implement frame 21. The implement frame 21 includes a front tool bar 36 supporting multiple tines 38, in the illustrated embodiment. The tines 38 are configured to contact the agricultural field 30 to condition the soil and prepare the agricultural field 30 for planting.

The structural members of the agricultural implement 16, such as the frame 21 and the hitch assembly 32, may be made of any suitable material, such as structural steel. In addition, leveling bars 42 are coupled to the implement frame 21, in the illustrated embodiment. The leveling bars 42 are configured to smooth the surface 22 of the agricultural field 30 in preparation for planting. Further, the implement 16 includes rolling baskets 44. The rolling baskets 44 are configured to condition the soil in preparation for planting via contact with the soil surface 22. In the illustrated embodiment, the rolling baskets 44 include a control system configured to selectively increase and decrease the force applied to the surface 22 via the rolling baskets 44. For example, as will be described below, an implement control system may send a signal to the rolling basket control system to increase the pressure applied by the rolling baskets 44. As a result, a hydraulic cylinder of the rolling basket control system may apply a greater force to the rolling baskets 44, thus inducing the rolling baskets to apply a greater pressure to the surface 22.

Figure 4:
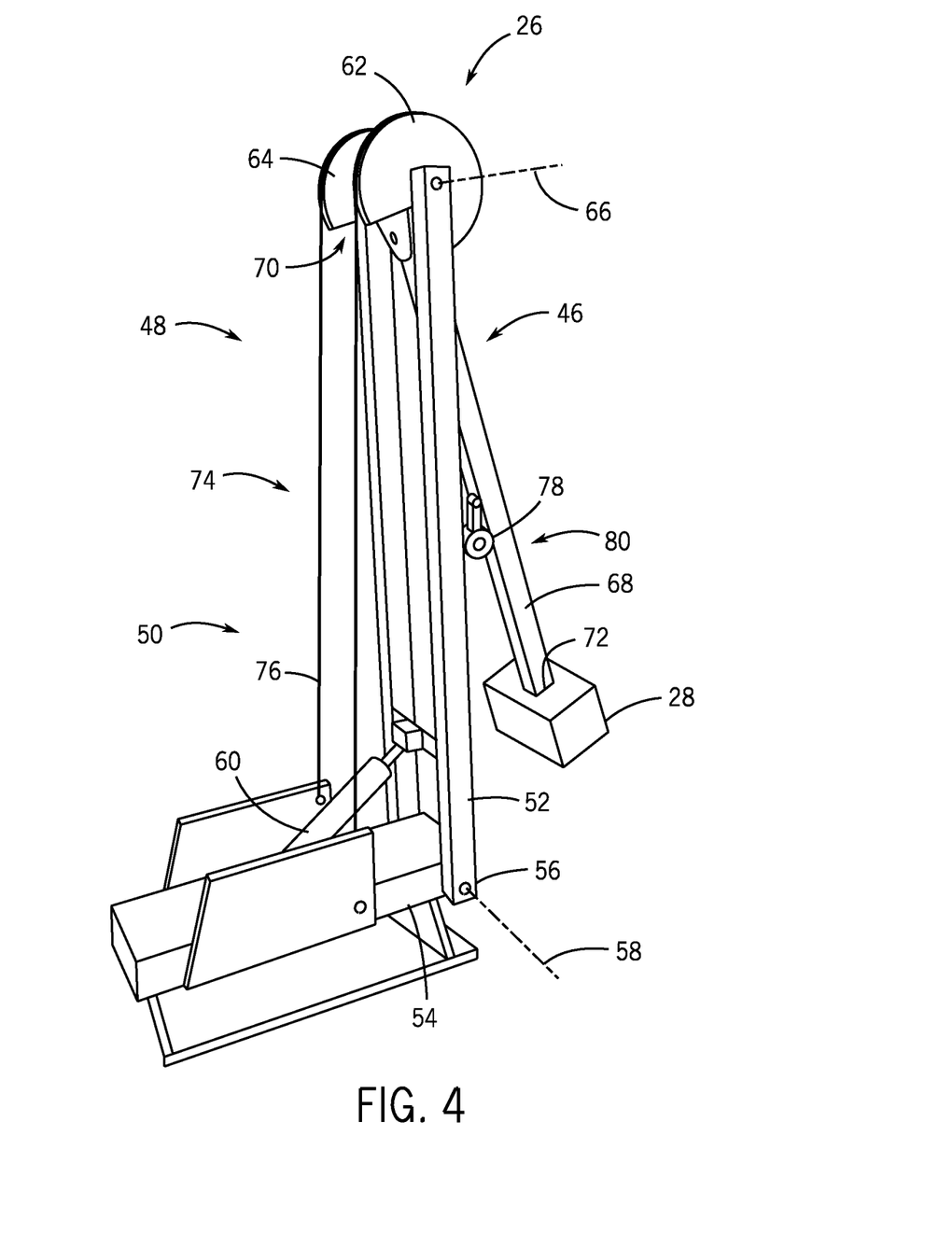
FIG. 4 is a perspective view of an embodiment of a soil analyzer assembly that may be utilized to adjust a position of a soil analyzer.

FIG. 4 is a perspective view of an embodiment of the mounting assembly 26 of the soil analyzer assembly 14, in which the mounting assembly is in a stored position 46. As will be described in detail below, the mounting assembly 26 is foldable or collapsible and configured to position the analyzer 28 proximate to the surface 22 of the agricultural field 30. The mounting assembly 26 includes a frame assembly 48, in the illustrated embodiment. Moreover, the frame assembly 48 includes frame members 50, as described in detail below. In the stored position 46, the analyzer 28 is deactivated. That is, data acquisition does not begin until the analyzer 28 is proximate to the surface 22 of the agricultural field 30. Moreover, a first support arm 52 (e.g., frame member 50) of the mounting assembly 26 is substantially perpendicular to the agricultural field 30 while the mounting assembly 26 is in the stored position 46. As shown, the first support arm 52 is rotatably coupled to the hitch 18 at a base 54. The base 54 is configured to secure the mounting assembly 26 to the hitch 18 or to any other suitable structure. In the illustrated embodiment, the first support arm 52 is coupled to the base 54 at a first end 56 of the first support arm 52. As mentioned above, the mounting assembly 26 is in the stored position 46 in FIG. 4. As a result, the first support arm 52 is in a substantially vertical orientation relative to the ground. However, the first support arm 52 is configured to rotate about a first axis 58. As discussed in detail below, rotation of the first support arm 52 about the first axis 58 transitions the mounting assembly 26 between the stored position 46 and an operation position in which the analyzer 28 is positioned rearward of the tow vehicle 12 and proximate to the soil surface. However, as mentioned above, in embodiments in which the assembly 14 is mounted forward of the tow vehicle 12, moving the mounting assembly 26 to the operation position places the analyzer 28 in front of the tow vehicle 12 (e.g., moves the analyzer 28 in the direction of travel 24 relative to the tow vehicle 12).

As mentioned above, the first support arm 52 rotates about the first axis 58 to transition the mounting assembly 26 between the stored position 46 and an operation position. In the illustrated embodiment, an actuator 60 drives the first support arm 52 to rotate about the first axis 58. As shown, the actuator 60 is a hydraulic cylinder configured to extend and retract a piston rod coupled to the first support arm 52 to drive rotation about the first axis 58. For example, when the piston rod is refracted, the first support arm 52 is driven toward the stored position 46 and when the piston rod is extended the first support arm 52 is driven toward the operation position. However, it should be appreciated that alternative linear actuators (e.g., screw drives, electromechanical actuators, etc.) may be employed in alternative embodiments. In further embodiments, a rotary actuator (e.g., hydraulic, electrical, etc.) may be used. In certain embodiments, a gear and pulley system may be utilized to drive rotation of the first support arm 52. Moreover, as will be discussed in detail below, a control system may be included to control operation of the actuator 60.

The mounting assembly 26 also includes a rotation member 62 rotatably coupled to the first support arm 52 at a second end 64. In the illustrated embodiment, the rotation member 62 is configured to rotate about a second axis 66. Moreover, the rotation member 62 is coupled to a second support arm 68 at a first end 70 of the second support arm 68. The second support arm 68 is configured to rotate about the second axis 66 relative to the first support arm 52. That is, the second support arm 68 rotates about the second axis 66 with the rotation member 62. The second support arm 68 is configured to support the analyzer 28 at a second end 72 of the second support arm 68. As a result of this configuration, the analyzer 28 is moved toward the position rearward of the tow vehicle 12 and proximate to the soil surface 22 as the first support arm 52 and the second support arm 68 are moved to the operation position. As mentioned above, in embodiments where the mounting assembly 26 is mounted on the front of the tow vehicle 12, the analyzer is moved toward the position forward of the tow vehicle 12 and proximate to the soil surface 22 as the first support arm 52 and the second support arm 68 are moved to the operation position.

In the illustrated embodiment, an actuator 74 drives the second support arm 68 to rotate about the second axis 66. As shown, the actuator 74 includes cables 76 extending from the base 54 to the rotation member 62. However, in certain embodiments alternative linear actuators (e.g., screw drives, electromechanical actuators, etc.) may be employed. For instance, a hydraulic cylinder may be coupled to the second support arm 68 to drive rotation about the second axis 66. In further embodiments, a rotary actuator (e.g., hydraulic, electrical, etc.) may be used. In certain embodiments, a gear and pulley system may be utilized to drive rotation of the first support arm 52. Moreover, as will be discussed in detail below, a control system may be included to control operation of the actuator 74. The cables 76 drive the rotation member 62 to rotate about the second axis 66 as the first support arm 52 rotates about the first axis 58. That is, tension in the cables 76 increases as the first support arm 52 rotates about the first axis 58, and that tension is applied to the rotation member 62 to drive the rotation member 62 to rotate about the second axis 66. As a result, the second support arm 68 also rotates about the second axis 66. Furthermore, the cables 76 may be straps, ropes, or any suitable structure capable of applying force to the rotation member 62 and/or to the second support arm 68. Therefore the load placed on the tow vehicle 12 is reduced. Moreover, the mechanical connections of the cables 76 provide reliable operation while enabling relatively simple maintenance.

In the illustrated embodiment, a support wheel 78 is rotatably coupled to the second support arm 68. The support wheel 78 is positioned on the second support arm 68 such that the support wheel 78 is in a retracted position 80 while the mounting assembly 26 is in the stored position 46 and in a lowered position while the mounting assembly 26 is in the operation position. Accordingly, the position of the support wheel 78 corresponds to the position of the second support arm 68. As discussed below, the support wheel 78 is configured to distribute the weight of the second support arm 68 and the analyzer 28 while the mounting assembly 26 is in the operation position. Moreover, the support wheel 78 is sized to place the analyzer 28 proximate to the surface 22 of the agricultural field 30 while the mounting assembly 26 is in the operation position. As a result, the support wheel 78 enables the analyzer 28 to monitor the soil without contacting the surface 22 of the agricultural field 30. Moreover, the support wheel 78 distributes the weight of the second support arm 68 and actuator 74, thereby enabling longer lengths of the first support arm 52 and second support arm 68. It is appreciated that while one support wheel 78 is shown in the illustrated embodiment, the second support arm 68 and/or the first support arm 52 may include additional support wheels 78 in alternative embodiments. Moreover, as described below, multiple sleds or other support devices may be included in certain embodiments. Furthermore, in certain embodiments, support structures are not included.

Figures 5, 6:
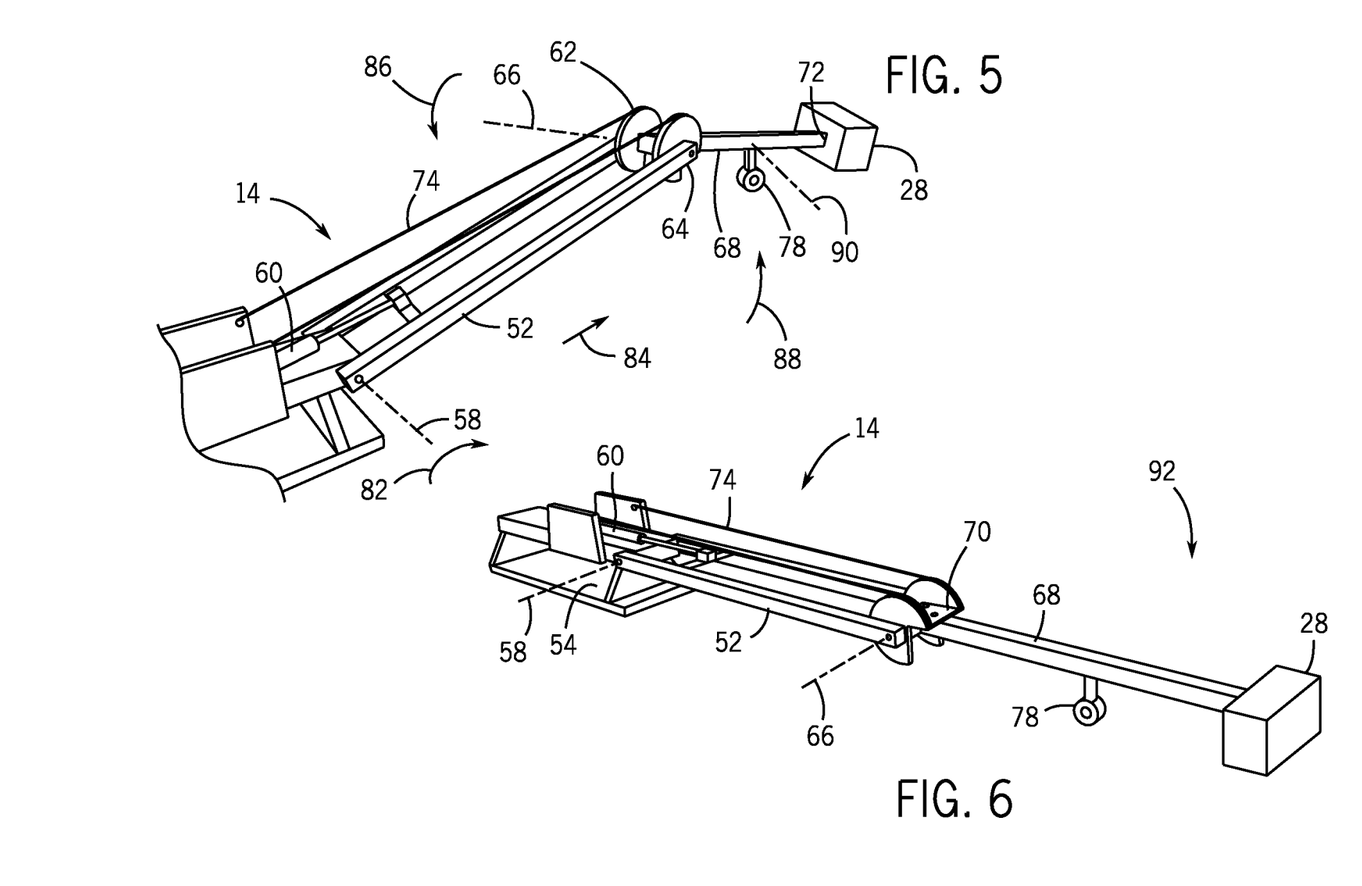
FIG. 5 is a perspective view of the soil analyzer assembly of FIG. 5, in which a mounting assembly is positioned between a stored position and an operation position.
FIG. 6 is a perspective view of the soil analyzer assembly of FIG. 5, in which the mounting assembly is positioned in the operation position.

FIG. 5 is a perspective view of the mounting assembly 26 in an intermediate position between the stored position 46 and the operation position. In the illustrated embodiment, the first support arm 52 rotates about the first axis 58 via the actuator 60 in a first direction 82, thereby moving the second end 64 of the first support arm 52 in a longitudinal direction 84 that is opposite the direction of travel 24 of the agricultural implement 16. As the first support arm 52 rotates about the first axis 58, the second end 64 of the first support arm 52 moves closer to the surface 22 of the agricultural field 30. Moreover, in the illustrated embodiment, the second support arm 68 is driven to rotate about the second axis 66 in a second direction 86 by the actuator 74 (e.g., cables 76). As shown, the second direction 86 is opposite the first direction 82. Rotation in the second direction 86 drives the second end 72 of the second support arm 68 to move in the longitudinal direction 84. As a result, the mounting assembly 26 is elongated as the mounting assembly 26 transitions to the operation position, thereby moving the agricultural soil analyzer 28 rearwardly. However, as mentioned above, in certain embodiments the mounting assembly 26 may be positioned at the front of the tow vehicle 12 or in front of the agricultural implement 16, and therefore the transition to the operation position moves the agricultural soil analyzer 28 in the same direction as the direction of travel 24 (e.g., opposite the longitudinal direction 84).

As mentioned above, the second support arm 68 includes the support wheel 78 configured to transition between the retracted position 80 while the mounting assembly 26 is in the stored position 46 and a lowered position 88 while the mounting assembly 26 is in the operation position. In the illustrated embodiment, the support wheel 78 is rotated about a wheel axis 90 as the second support arm 68 rotates about the second axis 66 in the second direction 86. The support wheel 78 is mounted to the second support arm 68 such that gravity pulls the support wheel to the lowered position 88 as the mounting assembly 26 transitions to the operation position. Additionally, the support wheel 78 rotates back to the retracted position 80 as the mounting assembly 26 transitions toward the stored position 46.

FIG. 6 is a perspective view of the mounting assembly 26 in an operation position 92. As described above, the first support arm 52 is driven about the first axis 58 in the first direction 82 by the actuator 60. In the operation position 92, the first support arm 52 is substantially parallel to the surface 22 of the agricultural field 30. Moreover, the second support arm 68 is driven about the second axis 66 in the second direction 86 by the actuator 74. As a result, the second support arm 68 is oriented substantially parallel to the surface 22 of the agricultural field 30. Furthermore, the support wheel 78 contacts the surface 22 of the agricultural field 30 to support the weight of the mounting assembly 26 in the operation position 92.

As shown, in the illustrated embodiment, the analyzer 28 is proximate to the surface 22 of the agricultural field 30 while the mounting assembly 26 is in the operation position 92. As a result, the analyzer 28 is positioned to emit and/or receive acoustic energy into/from the soil without contacting the surface 22 of the agricultural field 30. Furthermore, in the illustrated embodiment, the mounting assembly 26 extends in the longitudinal direction 84. As illustrated, the mounting assembly 26 extends from the soil analyzer assembly 14 in a rearward direction relative to the direction of travel 24 of the tow vehicle 12. Moreover, additional support wheels 78 may be coupled to the first support arm 52 and/or to the second support arm 68 to support the mounting assembly 26 in embodiments having assemblies that extend farther distances from the tow vehicle 12. Furthermore, multiple mounting assemblies 26 and analyzers 28 may be coupled to the agricultural implement 16. For example, mounting assemblies 26 may be mounted across the front end of the tow vehicle 12, the rear end of the tow vehicle 12, and/or the agricultural implement 16, such that the analyzers 28 span the length of the agricultural implement 16. Additionally, while the illustrated embodiment shows one analyzer 28 coupled to the mounting assembly 26, it is understood that multiple analyzers 28 may be coupled to the mounting assembly 26 at various locations along the first support arm 52 and/or the second support arm 68. Furthermore, in certain embodiments, the mounting assembly 26 may include additional frame members 50 mounted perpendicular to the direction of travel 24. That is, the frame members 50 may extend across the width of the tow vehicle 12. As a result, multiple analyzers 28 may be mounted across the width of the tow vehicle 12 and/or the implement 16 via the additional frame members 50. Moreover, as mentioned above, in certain embodiments the mounting assembly 26 may extend in a forward direction relative to the direction of travel 24 of the tow vehicle 12.

In other embodiments, the mounting assembly 26 may include a ramp to move the analyzer 28 rearwardly and proximate to the surface of the agricultural field 30. For example, the analyzer 28 may be coupled to an analyzer member that rolls down the ramp, which is coupled to the hitch 18. A wheel or sled may support the analyzer member against the surface of the agricultural field 30 while the analyzer 28 is positioned proximate to the surface 22 of the agricultural field 30. The analyzer member may be coupled to the ramp via a cord, and a pulley system may be used to drive the analyzer 28 and analyzer member up the ramp for storage and transportation. Moreover, in another embodiment, the analyzer 28 may be coupled to the end of a linear actuator (e.g., hydraulic cylinder). The linear actuator may include a wheel or sled configured to contact the surface of the agricultural field 30 when the actuator is extended. Extension of the actuator may move the analyzer 28 away from the tow vehicle 12 and/or the agricultural implement 16 to the operation position. In a further embodiment, the mounting assembly 26 may include a single arm configured to rotate about the first axis 58. An actuator may transition the single arm between the stored position and the operation position.

Moreover, in alternative embodiments, the support wheel 78 may be replaced by a sled coupled to the second support arm 68 via a parallel linkage. That is, the sled may contact the surface 22 of the agricultural field 30 to support the second support arm 68 as the analyzer 28 is transitioned to the operation position 92. Furthermore, the sled may be configured to block contact between the analyzer 28 and the surface 22. It will be appreciated that other mechanisms may be employed to support the second support arm 68 while blocking contact between the analyzer 28 and the surface 22. For instance, the second support arm 68 may include support arms that contact the frame 20 of the soil analyzer assembly 14 to suspend the analyzer 28 above the surface 22 of the agricultural field 30. Moreover, in certain embodiments, the soil analyzer assembly 14 may include a support structure to suspend the analyzer 28 over the surface 22 of the agricultural field 30 without movement between the stored position 46 and the operation position 92. For instance, the soil analyzer assembly 14 may include cross braces between frame members of the frame 21 to support the weight of the analyzer 28.

As discussed above, the analyzer 28 may be supported and moved into the operation position 92 by the mounting assembly 26. Moreover, the mounting assembly 26 may support the analyzer 28 in the stored position 46 during transportation or non-analysis conditions. Furthermore, the mounting assembly 26 is configured to position the analyzer 28 proximate to the surface 22 of the agricultural field 30, thereby enabling data collection via emission and/or reception of acoustic waves. Additionally, as mentioned above, the mounting assembly 26 is configured to be positioned either in front of the tow vehicle 12, behind the tow vehicle 12, or in front of the agricultural implement 16, thereby enabling control of soil conditioning operations and/or tow vehicle 12 operations in real-time or near real-time, as will be discussed in detail below.

Figure 7:
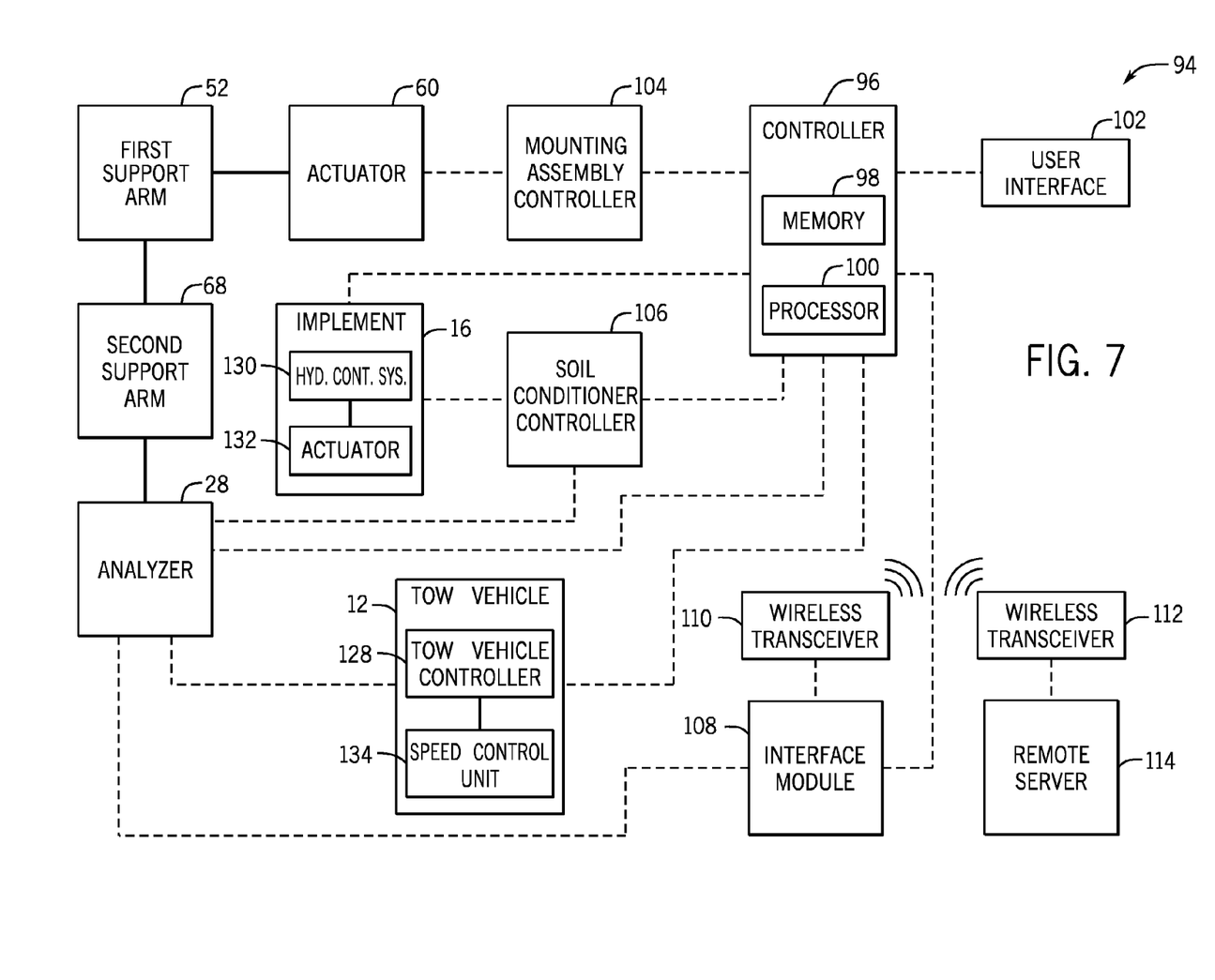
FIG. 7 is a block diagram of an embodiment of a control system for controlling an agricultural system.

FIG. 7 is a block diagram of an embodiment of a control system 94 configured to control the agricultural system 10. In the illustrated embodiment, the control system 94 includes a controller 96 having a memory 98 and a processor 100, and a user interface 102. The memory 98 may be any type of non-transitory machine readable medium for storing data and executable instructions, such as random-access memory, read-only memory, rewritable flash memory, hard drives, optical discs, and the like. The processor 100 may execute instructions stored on the memory 98. For example, the memory 98 may contain machine readable code, such as instructions, that may be executed by the processor 100. In some embodiments, the memory 98 and processor 100 may enable automatic (e.g., processor/memory controlled) operation of the mounting assembly 26, tow vehicle 12, and/or the agricultural implement 16.

The operator may interact with the user interface 102 (e.g., via push buttons, dials, touch screen interfaces, etc.) to send an operation signal to the controller 96. For example, the operator may depress a button on the user interface 102 that sends the operation signal to the controller 96 indicative of a command to drive the mounting assembly 26 into the operation position 92. As mentioned above, the processor 100 may execute instructions stored on the memory 98. The controller 96 is configured to send a control signal to a mounting assembly controller 104 to drive the mounting assembly 26 to the operation position 92. For example, the mounting assembly controller 104 may include a hydraulic control system having valves that control hydraulic fluid flow to the actuator 60. Directing the valve to open provides fluid to the actuator 60 which drives the first support arm 52 to rotate in the first direction 82 about the first axis 58. As described above, rotation of the first support arm 52 in the first direction 82 also drives rotation of the second support arm 68 in the second direction 86 via the actuator 74. Therefore, interaction with the user inference 102 may facilitate the transition of the mounting assembly 26 from the stored position 46 to the operation position 92. In certain embodiments, the mounting assembly controller 104 may also control the actuator 74. Moreover, in certain embodiments, the controller 96 may send a signal to the analyzer 28 to activate and begin data collection when the mounting assembly 26 reaches the operation position 92 (e.g., via sensors on the mounting assembly detecting the position of the first support arm 52 and/or the second support arm 68). As will be appreciated, a similar operation may transition the mounting assembly 26 from the operation position 92 to the stored position 46 and deactivate the analyzer 28.

As shown in FIG. 7, data acquired by the analyzer 28 may be output to a soil conditioner controller 106, an interface module 108, a tow vehicle controller 128, and/or the controller 96. For example, the analyzer 28 may output a first signal indicative of a parameter of the soil and/or the surface 22. In certain embodiments, the parameter is the roughness (e.g., a value that is above a predetermined value stored in the memory 98) of the surface 22 to the controller 96. Upon receiving the first signal, the controller 96 may determine a target parameter to adjust based on the signal. In certain embodiments, the controller 96 is configured to determine a target pressure (e.g., via a table, an algorithm, or the like) based on the first signal received from the analyzer 28. Additionally, in other embodiments, the controller 96 may determine different target parameters. For example, the controller 96 may determine a soil penetration depth for a tillage implement. The controller 96 may output a second signal indicative of the target parameter (e.g., pressure, soil penetration depth, etc.) to the soil conditioner controller 106. Accordingly, the soil conditioner controller 106 may output a third signal to a hydraulic control system 130 of the implement 16 to apply greater pressure to the surface 22 (e.g., by sending more hydraulic fluid to the actuator 132 controlling the rolling baskets 44). While the illustrated embodiment includes the soil conditioner controller 106, in other embodiments the soil conditioner controller 106 be configured to control a tillage implement, or the like.

In certain embodiments, the analyzer 28 may continuously send signals to the controller 96 indicative of the surface roughness. Moreover, the controller 96 may adjust the pressure applied to the surface 22, the speed of the agricultural system 10, or a combination of the two. To that end, surface roughness data may be continuously evaluated to provide real-time or near real-time control of the soil conditioner pressure or the tow vehicle speed to reduce soil compaction and/or enhance soil conditioning during soil conditioning operations.

Moreover, in certain embodiments, the analyzer 28 may output data to the interface module 108 for collection, storage, and/or further analysis. In some embodiments, the interface module 108 may interface with an ISOBUS network. However, in other embodiments, the interface module 108 may interface with a CAN bus network, data processing software, or the like. For instance, the interface module 108 may be communicatively coupled to a wireless transceiver 110 configured to wirelessly (e.g., via cellular signals, 4G, Wi-Fi, or the like) output data to a second wireless transceiver 112 communicatively coupled to a remote sever 114. However, in other embodiments, the data may be transferred via wired transmitters (e.g., USB, category 5, etc.) or removable storage devices (e.g., USB memory sticks, portable hard drives, etc.). The remote sever 114 (e.g., remote storage database, cloud database, etc.) may store the data for later analysis. For instance, transfer of the data to the remote server 114 enables access to the data to facilitate preparation of soil maps concurrently with monitoring the soil, thereby reducing the time between data acquisition and fertilizing/planting operations. For instance, in certain embodiments the soil analyzer assembly 14 may conduct measurement and data analysis in one pass and then a subsequent soil conditioning pass may use the data acquired by the analyzer 28. However, in other embodiments, software configured to generate three dimensional field maps may be loaded onto the memory 98, and the processor 100 may generate maps in real-time and/or near real-time during data acquisition, as described above. Accordingly, tillage operations may be performed and/or planned during data acquisition (e.g., planned during the same data acquisition pass).

As noted above, in certain embodiments, multiple soil analyzers 28 may be communicatively coupled to multiple rolling baskets 44 to facilitate soil conditioning operations. For example, the system 10 may include an equal number of soil analyzers 28 and rolling baskets 44. Accordingly, the rolling baskets 44 may be individually controlled (e.g., pressure increased or decreased) via the soil conditioner controller 106 based on the data received from the soil analyzers 28. During conditioning operations, sections of the surface 22 may have different roughness values. For example, the multiple soil analyzers 28 may send signals to the controller 96 indicative of the roughness values of multiple swaths of soil. The controller 96 may send signals to the soil conditioner controller 106 indicative of the roughness values of the soil. As a result, the soil conditioner controller 106 may send signals to the hydraulic control system 130 to instruct the actuators 132 to urge the multiple rolling baskets 44 toward the surface 22 based on the different roughness values of the swaths of soil. As a result, different rolling baskets 44 may apply different pressures to the soil 22 based on the measurements of the respective soil analyzers 28. By analyzing the surface 22 at multiple points during a single pass, the individual rolling baskets 44 may condition different sections of the surface 22 differently. For example, the soil in front of each rolling basket 44 may vary in roughness and, as a result, the rolling baskets 44 may apply different pressures to the surface 22 to condition the soil. Accordingly, over-conditioning of the surface 22 may be reduced or eliminated by taking measurements of surface roughness at different sections across the implement 16 and individually adjusting the rolling baskets 44 accordingly.

In certain embodiments, data acquired by the analyzer 28 may also be used to adjust operating parameters of the tow vehicle 12. For example, in certain embodiments, the controller 96 receives the first signal from the analyzer 28. The controller 96 is configured to determine a target speed of the agricultural system 10 based on the first signal (e.g., via a table stored in the memory 98, an algorithm, etc.). The controller 96 outputs a second signal indicative of the target speed to the tow vehicle controller 128 of the tow vehicle 12. In certain embodiments, the tow vehicle controller 128 is configured to output a third signal to a speed control unit 134 to adjust the speed of the tow vehicle 12. For example, the controller 96 may decrease the speed of the tow vehicle 12 while the surface 22 has a high roughness value.

While the preceding embodiments have been described in terms of soil conditioning (e.g., tillage) implements, the data acquired by the analyzer 28 may be used during other operations. For instance, during planting operations, cutters (e.g., ground engaging tools) that ameliorate the soil in preparation for deep deposition may be configured to penetrate the surface 22 of the soil at a greater depth to account for the compaction of the soil. For example, the analyzer 28 may send the first signal to the controller 96 indicative of a level of compaction of the soil. The controller 96 may determine a target cutter pressure (e.g., down pressure) sufficient to penetrate the soil to a desired depth. In certain embodiments, the controller 96 outputs the second signal to the soil conditioning control system 106 indicative of the target cutter pressure. As a result, the soil conditioner controller 106 sends the third signal to the implement 16 (e.g., to the hydraulic control system 118) to increase and/or decrease the pressure applied to the cutters. Moreover, the speed of the tow vehicle 12 may be increased or decreased based on data obtained by the analyzer 28. It will be appreciated that the data acquired by the analyzer 28 may be used during soil conditioning, planting, fertilizing, and the like.

Figure 8:
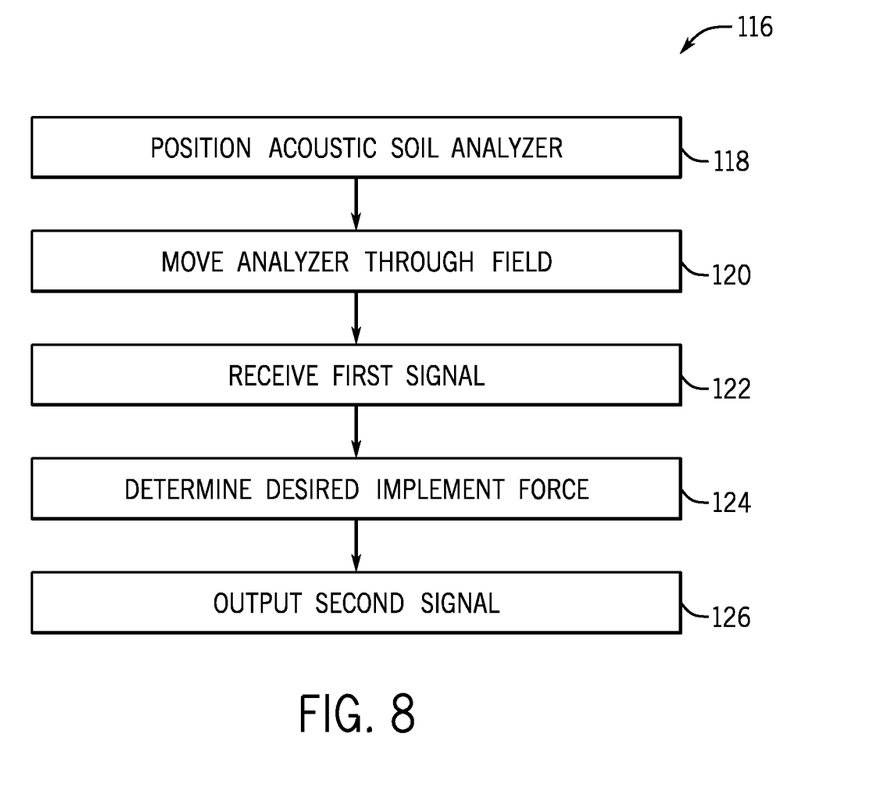
FIG. 8 is a flow chart of an embodiment of a method for controlling an agricultural system.

FIG. 8 is a flowchart of an embodiment of a method 116 for conducting data acquisition using the agricultural soil analyzer 28. The analyzer 28 is positioned proximate to the surface 22 at block 118. That is, the mounting assembly 26 is moved from the stored position 46 to the operation position 92. For example, the actuator 60 may drive rotation of the first support arm 52 in the first direction 82 and the actuator 74 may drive rotation of the second support arm 68 in the second direction. Moreover, in some embodiments, the control system 94 may send a signal to the actuator 60 to control rotation of the mounting assembly 26 between the stored position 46 and the operation position 92. The analyzer 28 is positioned forward of the soil conditioner 16. In certain embodiments, the analyzer 28 may be positioned behind the tow vehicle 12. However, in other embodiments, the analyzer 28 is positioned in front of the tow vehicle 12. The tow vehicle 12 moves the soil analyzer assembly 14 through the agricultural field 30 while the mounting assembly 26 is in the operating position 92 at block 120.

The analyzer 28 emits and/or receives acoustic waves to/from the surface 22 of the soil while being towed through the agricultural field 30. Furthermore, a first signal indicative of a value of soil roughness is sent to and received by the control system 94 (e.g., the controller 96, the soil conditioner controller 106, or the like) at block 122. That is, the data acquired by the analyzer 28 is received by a control device. For instance, the analyzer 28 may output the data to the controller 96, the soil conditioner controller 106, and/or the interface module 108. In certain embodiments, raw data (e.g., unprocessed data) is used during analysis by the analyzer 28 and/or the controller 96. In other embodiments, the controller 96 may determine the value indicative of surface roughness based on operations performed by the processor 100. For example, software may analyze the data acquired by the analyzer 28 and determine the magnitude of the surface roughness. The controller 96 may then determine a target pressure for the soil conditioner of the implement 16 (e.g., a pressure applied by the soil conditioner to the surface 22) at block 124. For instance, the controller 96 may determine that the pressure is lower than desired based on the roughness of the surface 22. However, the controller 96 may determine that the pressure is greater than desired or is appropriate for the surface roughness. As a result, the controller 96 may send a signal to the soil conditioner controller 106 to increase or decrease the pressure applied by the soil conditioner to the surface 22.

Accordingly, the control device may generate output signals to control operations of the tow vehicle 12, agricultural implement 16, or the like at block 126. For instance, the soil conditioner controller 106 may send a signal to the hydraulic control system 130 of the implement 16 to increase the pressure applied to the surface 22 of the agricultural field by the rolling baskets 44. Furthermore, in certain embodiments, the controller 96 may adjust the speed of the agricultural system 10. For instance, the controller 96 may send the second signal to the tow vehicle controller 116 of the tow vehicle 12. The second signal may be indicative of a command to reduce the speed of the work vehicle 12. The tow vehicle controller 128 may output the third signal to the speed control unit 134 to adjust the speed of the tow vehicle 12 based on the second signal. As a result, the speed of the agricultural system 10 may be adjusted based on the first signal sent to the controller 96 by the analyzer 28. Moreover, in certain embodiments, the interface module 108 may transmit the soil roughness data to the remote server 114 for analysis and/or storage. As mentioned above, a similar process may be used to adjust the speed of the tow vehicle 12, the depth of cutting tools during planting operations, and the like.

As described in detail above, the disclosed embodiments include a mounting assembly 26 configured to selectively position the agricultural soil analyzer 28 in the operation position 92, thereby positioning the agricultural soil analyzer 28 proximate to the surface 22 of the agricultural field 30. In certain embodiments, the operation position 92 places the analyzer 28 longitudinally rearward of the tow vehicle 12. However, in other embodiments, the operation position 92 places the analyzer 28 longitudinally forward of the tow vehicle 12. While in the operation position, the analyzer 28 emits acoustic waves into the soil and monitors the energy returned from the soil. The data obtained from the analyzer 28 is analyzed and/or relayed to the control system 94 to enhance tillage operations. For instance, the analyzer 28 may receive data indicating a high surface roughness and, upon receiving the data from the analyzer 28, the controller 96 may send a signal to the soil conditioning control system 106 directing the hydraulic control system 130 to increase the pressure applied to the surface 22 of the agricultural field 30 (e.g., by directing the hydraulic cylinder to extend a piston rod) by the rolling basket 44. As a result, real-time or near real-time adjustments may be made during soil conditioning operations to enhance and/or improve soil compaction. Moreover, the data may be uploaded to a database for further analysis.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An agricultural system, comprising:
   a ground engaging tool configured to engage an agricultural field;
   an agricultural soil analyzer positioned forward of the ground engaging tool relative to a direction of travel of the agricultural system, wherein the agricultural soil analyzer is configured to output a first signal indicative of a parameter of soil forward of the ground engaging tool relative to the direction of travel; and
   a controller communicatively coupled to the agricultural soil analyzer, wherein the controller is configured to receive the first signal from the agricultural soil analyzer, and wherein the controller is configured to determine a target speed of the agricultural system based on the first signal and to output a second signal indicative of the target speed, to determine a target pressure of the ground engaging tool based on the first signal and to output a third signal indicative of the target pressure, to determine a target penetration depth of the ground engaging tool based on the first signal and to output a fourth signal indicative of the target penetration depth, or a combination thereof.

2. The agricultural system of claim 1, comprising a mounting assembly comprising a frame assembly coupled to the agricultural soil analyzer and configured to couple to a tow vehicle of the agricultural system, wherein the mounting assembly is configured to selectively position the agricultural soil analyzer relative to the tow vehicle.

3. The agricultural system of claim 2, wherein the mounting assembly is configured to position the agricultural soil analyzer longitudinally rearward of the tow vehicle.

4. The agricultural system of claim 2, wherein the mounting assembly is configured to position the agricultural soil analyzer longitudinally forward of the tow vehicle.

5. The agricultural system of claim 1, wherein the ground engaging tool comprises a soil conditioner having a rolling basket.

6. The agricultural system of claim 1, comprising a hydraulic cylinder coupled to the ground engaging tool and communicatively coupled to the controller, wherein the hydraulic cylinder is configured to adjust the pressure of the soil conditioner based on the third signal.

7. The agricultural system of claim 1, comprising an interface module configured to output the second signal via a wireless transmitter.

8. The agricultural system of claim 2, wherein the mounting assembly comprises:
   a base configured to couple to the tow vehicle;
   a frame configured to support the soil analyzer, wherein the soil analyzer is an acoustic soil analyzer configured to emit acoustic waves against the soil surface and to receive reflected waves; and
   an opening disposed in the frame such that the soil analyzer passes through the opening when the mounting assembly transitions the analyzer from a stored position to an operation position.

* * * * *